United States Patent [19]

Kearns

[11] Patent Number: 4,623,537
[45] Date of Patent: Nov. 18, 1986

[54] ORAL HYGIENE COMPOSITIONS

[75] Inventor: Nancye D. Kearns, Ossining, N.Y.

[73] Assignee: Union Carbide Corporation, Danbury, Conn.

[21] Appl. No.: 622,491

[22] Filed: Jun. 20, 1984

[51] Int. Cl.$^4$ ................................................ A61K 7/16
[52] U.S. Cl. ........................................ 424/49; 424/78
[58] Field of Search .................................. 424/49–58, 424/78

[56] References Cited

U.S. PATENT DOCUMENTS

| 2,501,145 | 3/1950 | Smith | 167/93 |
|---|---|---|---|
| 3,228,844 | 1/1966 | Strean | 167/93 |
| 3,689,637 | 9/1972 | Pader | 424/52 |
| 3,703,578 | 11/1972 | Cella et al. | 424/49 |
| 3,885,028 | 5/1975 | Cella et al. | 424/57 |
| 3,934,000 | 1/1976 | Barth | 424/49 |
| 3,954,962 | 5/1976 | Prussin | 424/49 |
| 4,343,785 | 8/1982 | Schmolka | 424/49 |
| 4,357,313 | 11/1982 | Harvey et al. | 424/52 |

OTHER PUBLICATIONS

Carbowax Trifunctional Polyethylene Glycol 990, Sep. 28, 1982.
Profit Center Profiles, Carbowax TPEG-990 (1974).

Primary Examiner—Shep K. Rose
Attorney, Agent, or Firm—Steven T. Trinker

[57] ABSTRACT

Organoleptic oral hygiene compositions comprise an oral hygiene active component in a vehicle comprising a polyfunctional polyethylene glycol having a weight average molecular weight of about 800 to 1500 and from 3 to about 8 hydroxyl groups.

9 Claims, No Drawings

ORAL HYGIENE COMPOSITIONS

This invention relates to oral hygiene compositions, and particularly such compositions containing vehicles that exhibit desirable properties such as consistency, stability, humectant and organoleptic properties.

BACKGROUND OF THE INVENTION

Oral hygiene compositions include dental cleaning compositions such as toothpastes, tooth gels and tooth creams; gum-treating compositions and mouth washes. These compositions must meet a number of demanding requirements such as providing the desired hygienic activity and exhibiting storage stability. Importantly, to be attractive, these compositions must also be organoleptic, i.e., be pleasant to use, especially in terms of consistency, smell, taste and color.

Polyethylene glycols have found use in oral hygiene compositions. For example, U.S. Pat. No. 4,357,313 discloses tooth paste compositions containing about 5 to 20% by weight of polyethylene glycol having an average molecular weight of about 900 to 1600 to prevent or reduce drying (plugging) of the composition in a toothpaste tube. Also, lower molecular weight polyethylene glycols, e.g., having a molecular weight of less than about 800, have been proposed as humectants for preventing hardening of a toothpaste. For example, see U.S. Pat. No. 3,689,637. Polyethylene glycols of higher molecular weight have also been proposed as binders for toothpastes and gels. See, for instance, U.S. Pat. Nos. 2,501,145 and 3,228,844. In U.S. Pat. No. 3,689,637, high molecular weight polyethylene glycols, e.g., having a molecular weight of about 800 to 20,000, is disclosed as being capable of providing desirable texture to the dentifrice.

Polyethylene glycols can, however, impart an undesirable taste to the oral hygiene compositions. U.S. Pat. No. 3,703,578, for instance, discloses the use of water in tooth cleaning compositions to "counteract or reduce possible adverse tastes that may otherwise tend to be imparted to the tooth paste by particular polyoxyalkyleneglycols which are utilized in said tooth pastes." (column 4, lines 60-63). Typically, the lower molecular weight polyethylene glycols, i.e., having a molecular weight below about 800, which are normally liquids, impart a bitter taste and a pronounced bitter after taste. With higher molecular weight polyethylene glycols, i.e., having a molecular weight above about 1200, the taste is relatively bland with no pronounced after taste, but these polymers are solid at room temperature, thereby restricting their usefulness in oral hygiene compositions. A solid polyethylene glycol may not impart the desired consistency to a composition. Also, restrictions in formulation can occur if the sought composition is a liquid, gel or paste which may not exhibit proper flow characteristics or stability under temperature conditions to which it may be subjected. Moreover, the higher molecular weight polyethylene glycols have lower humectant properties.

SUMMARY OF THE INVENTION

By this invention, oral hygiene compositions are provided which exhibit desirable organoleptic properties without undue effect on the other properties of the composition such as stability, consistency, viscosity, and hygroscopicity (humectancy). The compositions of this invention can be liquid or in the form of a gel or paste. Thus, this invention provides wide latitudes in product formulation.

In the oral hygiene compositions of this invention, an oral hygiene active component is provided in a vehicle comprising about 5 to 50 weight percent of a polyfunctional polyethylene glycol having a weight average molecular weight of about 800 to 1500 and from 3 to about 8 hydroxyl groups. Avantageously, the molecular weight of the polyfunctional polyethylene glycol is sufficient to provide a liquid at about 10° C., and sometimes at about 5° C.

The polyfuntional polyethylene glycols used in the compositions of this invention do not impart a bitter taste or noticeable bitter after taste to the oral hygiene composition, even when present in large amounts. Moreover, since the polyfunctional polyether can be in the liquid phase, it is capable of being used in a wide range of formulations, even as the predominant component of the vehicle. The liquid form also is advantageous in ingredient handling for the preparation of the composition. Further, the polyfunctional polyethylene glycols have desirable humectant properties.

DETAILED DESCRIPTION

Polyfunctional polyethylene glycols have at least three oxyalkylene-containing substituents which are terminated with hydroxyl groups. Particularly attractive polyfunctional polyethylene glycols can be represented by the formula $$R[(OCH_2CH_2)_nOH]_m$$

in which R is the organic residue of a polyfunctional alcohol having m hydroxyl groups wherein m is an integer of 3 to about 8, especially 3 to about 6, and often 3 or 4, and n is an integer of from about 3 to 10 or more. The number of oxyethylene groups for each of the m substituents may be the same or different. The oxyethylene chaining may also contain a minor proportion, often less than about 30 mole percent, of oxypropylene groups. Typically, the polyfunctional polyethylene glycol will comprise a mixture of species having different oxyethylene chain lengths.

The polyfunctional alcohol includes, for instance, glycerol; trimethylolpropane and other trimethylol alkane derivatives; pentaerythritol and di- and tripentaerythritol; manitol, sorbitol and other such naturally occurring polyols; trihydroxyheptane; 1,2,6-hexanetriol and the like. Glycerol is the preferred polyfunctional alcohol.

The polyfunctional polyethylene glycol may also be a branched chain structure such as disclosed in U.S. Pat. application Ser. No. 468,670, filed Feb. 22, 1983, herein incorporated by reference.

The weight average molecular weight of the polyfunctional glycol is generally between about 800 and 1500, preferably, about 900 to 1200. A commercially available trifunctional polyethylene glycol is available for Union Carbide Corporation, Danbury, Conn., as CARBOWAX 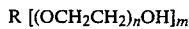 TPEG-990, a glycerol started polymer having an average molecular weight of about 990. This product has been proposed for use in the cosmetic, chemical specialty and pharmaceutical areas and has a low color and odor.

The oral hygiene compositions include mouth washes, gum treatment preparations, and tooth cleaning compositions and may be liquid, gelular, or pastes (semi-solid). The active ingredients and the amounts employed in the composition can vary broadly and include those ingredients and amounts conventionally employed in such hygiene compositions. The active ingredients can include antimicrobial ingredients, surfactants, detergents, soaps, abrasives, binders (viscosity modification agents), diluents and fillers such as water, perfumes, flavoring agents, colorants, buffers, preservatives, ionizable fluorine-containing compounds, enzymes, astringent salts, ethanol, humectants, and the like.

The amount of polyfunctional polyethylene glycol employed in the vehicle of the composition is from about 5 to 50 percent by weight. The amount used in a given product will depend upon the desired properties of the final product; however, because of the properties of the polyfunctional polyethylene glycols, this broad range can be accommodated. In many instances, the polyfunctional polyethylene glycol comprises about 10 to 30, e.g., about 10 to 25, weight percent of the vehicle.

Typical preparations employing the invention include the following (in weight percent):

|  | Broad Range | Preferred Range |
| --- | --- | --- |
| Mouthwashes |  |  |
| Active ingredients | 0.01% to 10% | 0.2% to 5% |
| Surfactants | 0 to 2% | 0.2% to 1% |
| Humectants (glycerol, sorbitol, etc.) | 0 to 50% | 1% to 20% |
| Polyfunctional polyethylene glycol | 5% to 30% | 10% to 20% |
| Water, ethanol, flavors, colorants, etc. | 99 to 100% | 99 to 100% |
| Tooth gels and pastes |  |  |
| Active Ingredients | 0.01% to 20% | 0.2% to 10% |
| Polishing agents | 0 to 70% | 10% to 60% |
| Foaming agents | 0 to 5% | 0.1% to 2% |
| Humectants (glycerol, sorbitol, etc.) | 0 to 70% | 0% to 30% |
| Polyfunctional polyethylene glycol | 5% to 50% | 10% to 40% |
| Water, flavors, | 0 to 30% | 0 to 20% |
| colorants, etc. |  |  |

It is claimed:

1. A oral hygiene composition comprising 0.01% to 20% weight percent of an oral hygiene active component in a liquid mouthwash, gelular gel, or semi-solid paste vehicle, said vehicle comprising about 5 to 50 weight percent of polyfunctional polyethylene glycol having a weight average molecular weight of about 800 to 1500 and from 3 to about 8 hydroxyl groups said polyethylene glycol being free of the bitter taste and pronounced bitter after taste typically imparted by the normally liquid lower molecular weight polyethylene glycols.

2. The composition of claim 1 wherein the oral hygiene composition is a gel.

3. The composition of claim 1 wherein the oral hygiene composition is a paste.

4. The composition of claim 1 wherein the oral hygiene composition is a liquid.

5. The composition of claim 1 wherein the polyfunctional polyethylene glycol is represented by the formula $$R 8 (OCH_2CH_2)_nOH]_m$$

wherein R is the organic residue of a polyfunctional alcohol having 3 to about 6 carbons and m is an integer of 3 to about 8 and is equal to the number of hydroxyls of the polyfunctional alcohol, n is an integer of from about 3 to 10 and may be the same or different for each of the substituents.

6. The composition of claim 5 wherein R is the residue of glycerol and m is 3.

7. The composition of claim 6 wherein the weight average molecular weight of the polyfunctional polyethylene glycol is about 900 to 1200.

8. The composition of claim 7 wherein the polyfunctional polyethylene glycol has a molecular weight such that it is liquid at about 10° C.

9. The composition of claim 1 wherein the polyfunctional polyethylene glycol has a molecular weight such that it is liquid at about 10° C.

* * * * *